United States Patent [19]
Kotani et al.

[11] Patent Number: 5,681,843
[45] Date of Patent: Oct. 28, 1997

[54] PARABANIC ACID DERIVATIVES

[75] Inventors: Takayuki Kotani; Kaoru Okamoto; Yasuhiro Nagaki, all of Hyogo, Japan

[73] Assignee: Nippon Zoki Pharmaceutical Co., Ltd., Osaka, Japan

[21] Appl. No.: 575,024

[22] Filed: Dec. 19, 1995

[30] Foreign Application Priority Data

Dec. 20, 1994 [JP] Japan .................... 6-335820

[51] Int. Cl.$^6$ .................. A10K 31/415; A01N 43/50; C07D 233/02; C07D 233/90
[52] U.S. Cl. .................. 514/386; 514/398; 548/317.5; 548/318.5; 548/165
[58] Field of Search .................. 548/317.5, 318.5, 548/165; 514/386, 398

[56] References Cited

U.S. PATENT DOCUMENTS

| | | |
|---|---|---|
| 4,096,130 | 6/1978 | Kraft et al. |
| 4,647,574 | 3/1987 | Ienaga et al. |
| 4,683,240 | 7/1987 | Ienaga et al. |
| 4,985,453 | 1/1991 | Ishii et al. |

FOREIGN PATENT DOCUMENTS

| | | |
|---|---|---|
| 0 353198 A1 | 1/1990 | European Pat. Off. |
| 26 12 926 A1 | 10/1977 | Germany |
| 2225485 | 9/1990 | Japan |
| WO 89/02890 | 4/1989 | WIPO |

OTHER PUBLICATIONS

"Pathologic Biochemistry and Clinics of Free Radicals, Inflammation and Antiinflammation," *Nippon Rinsho*, vol. 46, No. 10, pp. 93–97 (1988).

Yonnezawa, et al., *Nippon Kagaku Zasshi*, 89, No. 8, pp. 62–64 (1968.

Patton, *J. Org. Chem.*, 32, No. 2, pp. 383–388 (1967).

K. Ogawa, et al., "Synthesis of substituted 2, 4–dioxo–thienopyrimidin–1–acetic acids and their evaluation as aldose reductase inhibitors", *European Journal of Medicinal Chemistrychimica Therapeutica*, vol. 28, No. 10, 1993, pp. 769–781.

Morrison and Boyd, *Organic Chemistry*, Allyn and Bacon, Inc., Boston (1965), pp. 806, 808, 847–848.

*Primary Examiner*—Johann Richter
*Assistant Examiner*—Jane C. Osweeki
*Attorney, Agent, or Firm*—Fisher, Christen & Sabol

[57] ABSTRACT

Parabanic acid derivatives, pharmaceutically acceptable salts thereof, and therapeutic agents containing said compounds as an effective component are useful pharmaceuticals for the treatment of diabetic complications such as diabetic neuropathy, diabetic cataracts and retinopathy, diabetic nephropathy, diabetic dermopathy, and other diabetic microangiopathy. The compounds of the present invention are represented by the following general formula (I):

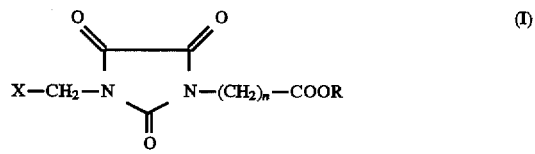

wherein R is hydrogen, lower alkyl or benzyl; X is substituted phenyl, optionally substituted benzothiazolyl, optionally substituted naphthyl, optionally substituted pyridyl, anthraquinonyl, phthalimide, or thienyl; and n is an integer from 1 to 3. The compounds of the present invention exhibit excellent inhibitory action towards aldose reductase with a high enzyme selectivity. Accordingly, they are useful as drugs for the therapy and prevention of various types of diabetic complications without substantially inhibitory aldehyde reductase.

19 Claims, No Drawings

PARABANIC ACID DERIVATIVES

FIELD OF THE INVENTION

The present invention relates to novel parabanic acid derivatives and pharmaceutically acceptable salts thereof, methods for making the derivatives and salts, and also to pharmaceutical compositions containing said compounds as the effective component.

BACKGROUND OF THE INVENTION

Diabetic neuropathy, diabetic cataracts and retinopathy, diabetic nephropathy, diabetic dermopathy and other diabetic microangiopathy have been known as chronic, difficult to treat diseases resulting from diabetes. Participation of a polyol metabolic system may be a cause of those diabetic complications.

Thus, when a hyperglycemic state results from diabetes, utilization of glucose via a polyol metabolic pathway increases several-fold compared with the normal state. Also, production of sorbitol by an aldose reductase is accelerated. It is presumed that, as a result thereof, intracellular sorbitol in peripheral nerves, retina, kidney, lens, artery and the like accumulates excessively. The excessive sorbitol accumulation leads to cell edema and hypofunction due to an abnormal osmotic pressure in the cells.

Accordingly, agents for inhibiting aldose reductase have been thought to be effective for the therapy and the prevention of diabetic complications and have been studied. However, conventional aldose reductase inhibitors are problematic because they strongly inhibit other enzymes which do not participate in the polyol metabolic pathway. For example, an aldehyde reductase may be undesirably inhibited by conventional aldose reductase inhibitors.

Under such circumstances, the present inventors have conducted a study to obtain inhibitors having a high enzyme selectivity toward aldose reductase which participates in the production of sorbitol with an object of providing therapy for and prevention of the above-mentioned diabetic complications. As a result, the present inventors have found that the parabanic acid derivatives of the present invention exhibit an excellent inhibitory action with a high enzyme selectivity to aldose reductase whereby the present invention has been achieved.

SUMMARY OF THE INVENTION

The parabanic acid derivatives and their pharmaceutically acceptable salts of the present invention exhibit unexpectedly superior selective inhibition of aldose reductase. The derivatives and their salts substantially inhibit aldose reductase and the production of intracellular sorbitol without substantial inhibition of other enzymes, such as aldehyde reductase which do not participate in the polyol metabolic pathway.

The compounds of the present invention include parabanic acid derivatives represented by the general formula (I) or pharmaceutically acceptable salts of the derivatives represented by the general formula (I):

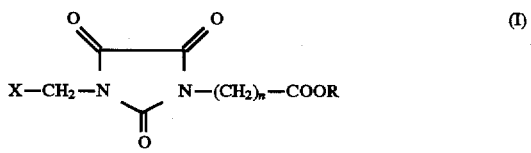

wherein

R is hydrogen, lower alkyl or benzyl;

X is phenyl which is substituted with trifluoromethyl, cyano, carboxy, carbamoyl, lower alkoxycarbonyl or both nitro and halogen, benzothiazolyl which may be substituted with at least one member selected from the group consisting of lower alkyl, lower alkoxy, trifluoromethyl, nitro, and halogen, naphthyl which may be substituted with nitro and/or substituted with halogen, pyridyl which may be substituted with nitro and/or substituted with halogen, anthraquinonyl, phthalimide, or thienyl; and n is an integer from 1 to 3.

The compounds of general formula (I) may be produced by condensing a compound represented by the general formula (II):

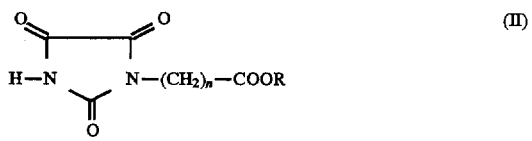

wherein R and n are defined as above, with a compound represented by the general formula (III):

wherein X is defined as above, and $R_1$ is hydroxyl, halogen, lower alkyl—$SO_2$—O—, or phenyl—$SO_2$—O— which may be substituted with lower alkyl. In preferred manufacturing methods, a compound of the general formula (II) in which R is lower alkyl is used in the condensation reaction to substantially reduce or essentially eliminate side reactions. In embodiments of the invention, the condensate obtained in the condensation reaction may be subjected to hydrolysis to obtain compounds wherein R is hydrogen.

The present invention also provides pharmaceutical compositions containing at least one of the derivatives of formula (I) or at least one salt thereof in a pharmaceutically acceptable amount.

The compounds and pharmaceutical compositions of the present invention may be used in pharmaceutically effective amounts to treat and prevent various types of diabetic complications such as diabetic neuropathy, diabetic cataracts and retinopathy, diabetic nephropathy, diabetic dermopathy and other diabetic microangiopathy.

DETAILED DESCRIPTION OF THE INVENTION

The present invention provides novel carboxyalkyl heterocyclic derivatives and pharmaceutically acceptable salts thereof having an excellent inhibitory action towards aldose reductase. The carboxyalkyl heterocyclic derivatives and their salts exhibit a high enzyme selectivity for aldose reductase thereby avoiding problems associated with the inhibition of other enzymes which do not participate in the polyol metabolic pathway. The derivatives and their pharmaceutically acceptable salts may be used in pharmaceutically effective amounts in therapeutic agents or pharmaceutical compositions for the treatment of diabetic complications.

The parabanic acid derivatives of the present invention are compounds which is represented by the following general formula (I):

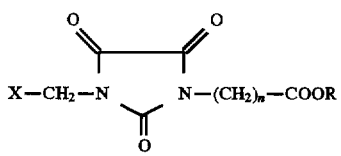

wherein

R is hydrogen, lower alkyl or benzyl;

X is phenyl which is substituted with trifluoromethyl, cyano, carboxy, carbamoyl, lower alkoxycarbonyl or both nitro and halogen, benzothiazolyl which may be substituted with lower alkyl, lower alkoxy, trifluoromethyl, nitro, halogen, or substituted with combinations thereof, naphthyl which may be substituted with nitro and/or substituted with halogen, pyridyl which may be substituted with nitro and/or substituted with halogen, anthraquinonyl, phthalimide, or thienyl; and n is an integer from 1 to 3.

The parabanic acid derivatives of the present invention may be, for example, prepared in accordance with the following method:

Thus, in a suitable solvent which does not disturb the reaction such as ethanol, acetone and N,N-dimetylformamide and in the presence of an alkali such as potassium hydroxide, potassium bicarbonate and sodium hydride, a compound of the general formula (II):

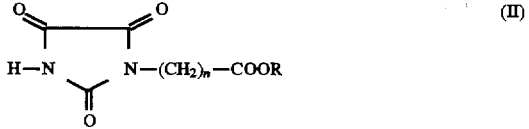

wherein R is hydrogen, lower alkyl or benzyl, and n is an integer from 1 to 3, is subjected to a condensation reaction to obtain a parabanic acid derivative represented by general formula (I). The condensation reaction is with a compound represented by the general formula (III):

X—CH$_2$—R$_1$ (III)

wherein

X is phenyl which is substituted with trifluoromethyl, cyano, carboxy, carbamoyl, lower alkoxycarbonyl or both nitro and halogen, benzothiazolyl which may be substituted with lower alkyl, lower alkoxy, trifluoromethyl, nitro, halogen, or substituted with combinations thereof, naphthyl which may be substituted with nitro and/or substituted with halogen, pyridyl which may be substituted with nitro and/or substituted with halogen, anthraquinonyl, phthalimide, or thienyl; and R$_1$ is hydroxyl, halogen, lower alkyl—SO$_2$—O—, or phenyl—SO$_2$—O— which may be substituted with lower alkyl.

In embodiments of the invention, the condensate may be subjected to hydrolysis to obtain a parabanic acid derivative represented by the general formula (I).

The condensation reaction may be carried out at room temperature or by heating to reflux depending upon the type of the alkali, solvent, and reactant used in the reaction.

In the case of compounds represented by the general formula (II) in which R is lower alkyl or benzyl, a conventional hydrolysis with an acid such as dissolution in a mixture of acetic acid and concentrated hydrochloric acid followed by heating to reflux is carried out after completion of the above-mentioned condensation whereupon the compound represented by the general formula (I) in which R is hydrogen can be prepared.

In preferred manufacturing methods, a compound of the general formula (II) in which R is lower alkyl is used to essentially eliminate side reactions.

In the above-mentioned general formulae (I) and (II), R is hydrogen; lower alkyl or, preferably, a linear or branched alkyl having 1 to 4 carbon atoms such as methyl, ethyl, propyl, isopropyl, butyl, isobutyl, sec-butyl and tert-butyl; or benzyl while n is an integer from 1 to 3. Preferably, n is 1.

In the above-mentioned general formulae (I) and (III), X may be phenyl which is substituted with trifluoromethyl, cyano, carboxy, carbamoyl, a linear or branched alkoxycarbonyl having 1 to 3 carbon atoms such as methoxycarbonyl, ethoxycarbonyl, propoxycarbonyl and isopropoxycarbonyl or both nitro and halogen such as fluorine, chlorine, bromine and iodine; benzothiazolyl which may be substituted with at least one member selected from the group consisting of a linear or branched alkyl having 1 to 3 carbon atoms such as methyl, ethyl, propyl and isopropyl, a linear or branched alkoxy having 1 to 3 carbon atoms such as methoxy, ethoxy, propoxy and isopropoxy, trifluoromethyl, nitro, and halogen such as fluorine, chlorine, bromine and iodine; naphthyl or pyridyl, either of which may be substituted with nitro and/or substituted with halogen such as fluorine, chlorine, bromine and iodine; anthraquinonyl; phthalimide; or thienyl.

In the above-mentioned general formula (III), R$_1$ is hydroxyl; halogen such as fluorine, chlorine, bromine and iodine; alkyl—SO$_2$—O— in which the alkyl may be a linear or branched alkyl having 1 to 3 carbon atoms such as methyl, ethyl, propyl and isopropyl; or phenyl—SO$_2$—O— which may be substituted with a linear or branched alkyl having 1 to 3 carbon atoms such as methyl, ethyl, propyl and isopropyl.

The parabanic acid derivatives of the present invention cover pharmaceutically acceptable salts of the compounds represented by the above-mentioned general formula (I). Exemplary salts of the compounds of general formula (I) are salts of the compounds of general formula (I) with an alkali metal such as sodium and potassium; with an alkali earth metal such as calcium and magnesium; with a metal such as aluminum, and with a base such as ammonia and organic amines.

The pharmaceutically acceptable salts may be manufactured, by conventional methods, starting from the parabanic acid derivatives of the present invention in free form or by conversion from one salt to another salt.

When there are stereoisomers such as cis-trans isomers, optical isomers and conformational isomers for the compounds of the present invention, or when the compounds exist as hydrates, the present invention covers any and all of such stereoisomers and hydrates.

The compounds of the present invention prepared as described above may be purified by conventional means such as distillation, chromatography and recrystallization.

The compounds may be identified by means of, for example, elementary analysis, melting point measurement, infrared (IR), nuclear magnetic resonance (NMR), and mass spectroscopy (MS).

The present invention is illustrated by the following examples wherein all parts, percentages and ratios are by weight, all temperatures are in °C., and all reactions are conducted at about atmospheric pressure unless indicated to the contrary:

EXAMPLE 1

Sodium hydride (0.89 g) was suspended in 10 mL of N,N-dimethylformamide, a solution of 3.53 g of ethyl 2,4,5-trioxoimidazolidine-3-acetate dissolved in 50 mL of N,N-dimethylformamide was dropped thereinto with stirring at not higher than 0° C. and then the mixture was stirred at room temperature for one hour. To the reaction mixture was added a solution of 3.78 g of 2-bromomethyl-5-trifluoromethyl-benzothiazole dissolved in 40 mL of N,N-dimethylformamide at not higher than 0° C. and the mixture was stirred for two hours more. The reaction solution was added to ice-cooled diluted hydrochloric acid and the mixture was stirred until it was solidified. The solid was filtered, washed with water and then with hexane and recrystallized from ethanol to give ethyl 3-[2-(5-trifluoromethylbenzothiazolyl)-methyl]-2,4,5-trioxoimidazolidine-1-acetate [Compound 1]. The melting point, IR, and NMR for the compound were:

Melting point: 150.0°–151.0° C.
IR(KBr): 3001, 1742(C=O), 1430, 1333, 1234, 1115 $cm^{-1}$
$^1$H-NMR(DMSO-$d_6$): 1.22(t,J=7.1Hz,3H,$CH_3$), 4.19(q,J=7.1Hz,2H,O-$CH_2$), 4.39 (s,2H,N—$CH_2$—$CO_2$), 5.33 (s,2H,$CH_2$—Ar), 7.80(d,J=8.4Hz,1H,Ar), 8.35(s,1H,Ar), 8.40(d,J=8.4Hz,1H,Ar)

EXAMPLE 2

Reactions similar to the synthesis of Compound 1 in Example 1 were carried out to give the following compounds:

Ethyl 3-(3-pyridylmethyl)-2,4,5-trioxoimidazolidine-1-acetate [Compound 2].
Melting point: 112.0°–113.0° C.
IR(KBr): 1730(C=O), 1450, 1425, 1230, 1145 $cm^{-1}$
$^1$H-NMR(DMSO-$d_6$): 1.20(t,J=7.0Hz,3H,$CH_3$), 4.16(q,J=7.0Hz,2H,O-$CH_2$), 4.39(s,2H,N—$CH_2$—$CO_2$), 4.79(s,2H,$CH_2$—N), 7.38(dd,J=8.0,4.5Hz,1H,Ar), 7.75(ddd,J=8.0,2.0,1.5Hz,1H,Ar), 8.51(dd,J=4.5,1.5Hz,1H,Ar), 8.57 (d,J=2.0Hz,1H,Ar)

Ethyl 3-(4-pyridylmethyl)-2,4,5-trioxoimidazolidine-1-acetate [Compound 3].
Melting point: 92.0°–94.0° C. (decomp.)
IR(KBr): 1740(C=O), 1720(C=O), 1520, 1440, 1400, 1230, 1140 $cm^{-1}$
$^1$H-NMR(DMSO-$d_6$): 1.21(t,J=7.0Hz, 3H,$CH_3$), 4.17 (q,J=7.0Hz ,2H,O-$CH_2$), 4.42(s,2H,N—$CH_2$—$CO_2$), 4.80(s, 2H,$CH_2$—N), 7.37 (d,J=5.5Hz, 2H,Ar), 8.54 (d,J=5.5Hz, 2H,Ar)

Benzyl 3-(2-thienylmethyl)-2,4,5-trioxoimidazolidine-1-acetate [Compound 4].
Melting point: 180.5°–182.5° C.
IR(KBr): 1734(C=O), 1448, 1431, 1207, 1146, 758 $cm^{-1}$
$^1$H-NMR(DMSO-$d_6$): 4.42(s,2H,N—$CH_2$—$CO_2$), 4.86(s, 2H,$CH_2$—N), 5.12(s,2H,O—$CH_2$), 6.94(dd,J=5.0,3.5Hz, 1H,Ar), 7.04(d,J=3.5Hz,1H,Ar), 7.29(s,5H,Ar), 7.51(d,J=5.0Hz,1H,Ar)

Ethyl 3-[3-(5-bromopyridyl)methyl]-2,4,5-trioxoimidazolidine-1-acetate [Compound 5].
Melting point: 137.0°–139.0° C.
IR(KBr): 1731(C=O), 1444, 1236, 1140, 1024 $cm^{-1}$
$^1$H-NMR (DMSO-$d_6$): 1.21(t, J=7.0Hz, 3H, $CH_3$), 4.16 (q, J=7.0Hz, 2H, O-$CH_2$), 4.40(s,2H,N—$CH_2$—$CO_2$), 4.82 (s,2H,$CH_2$—N), 8.06(dd,J=2.0,1.5Hz,1H,Ar), 8.58 (d,J=1.5Hz,1H,Ar), 8.64 (d,J=2.0Hz, 1H,Ar)

Ethyl 3-[3-(2-chloropyridyl)methyl]-2,4,5-trioxoimidazolidine-1-acetate [Compound 6].
Melting point: 131.0°–132.0° C.
IR(KBr): 1736(C=O), 1425, 1238, 1151, 1074 $cm^{-1}$
$^1$H-NMR(DMSO-$d_6$): 1.21(t,J=7.0Hz,3H,$CH_3$), 4.16(q,J=7.0Hz,2H,O-$CH_2$), 4.42(s,2H,N—$CH_2$—$CO_2$), 4.81(s, 2H,$CH_2$—N), 7.45(dd,J=7.5,4.5Hz,1H,Ar), 7.97(dd,J=7.5,1.5Hz,1H,Ar), 8.38 (dd, J=4.5,1.5Hz, 1H,Ar)
MS m/e: 325 ($M^+$)

Ethyl 3-[3-(6-chloropyridyl)methyl]-2,4,5-trioxoimidazolidine-1-acetate [Compound 7].
Melting point: 81.0°–83.0° C.
IR(KBr): 1732(C=O), 1448, 1234, 1028, 768 $cm^{-1}$
$^1$H-NMR(DMSO-$d_6$): 1.21(t,J=7.5Hz,3H,$CH_3$), 4.16(q,J=7.5Hz,2H, O-$CH_2$), 4.39 (s,2H,N—$CH_2$—$CO_2$), 4.81 (s,2H, $CH_2$—N), 7.53(d,J=8.0Hz,1H,Ar), 7.84(dd,J=8.0,2.5Hz,1H,Ar), 8.42 (d,J=2.5Hz, 1H,Ar)

Ethyl 3-(2-pyridylmethyl)-2,4,5-trioxoimidazolidine-1-acetate [Compound 8].
Melting point: 122.0°–123.0° C.
IR(KBr): 1734(C=O), 1448, 1236, 770, 513 $cm^{-1}$
$^1$H-NMR(DMSO-$d_6$): 1.21(t,J=7.0Hz,3H,$CH_3$), 4.17 (q,J=7.0Hz,2H, O-$CH_2$), 4.55 (s,2H,N—$CH_2CO_2$), 4.88(s,2H, $CH_2$—N ), 7.32(dd,J=7.5,4.5Hz,1H,Ar), 7.46(d,J=7.5Hz,1H,Ar), 7.81(dd,J=7.5,7.5Hz,1H,Ar), 8.50(d,J=4.5Hz,1H,Ar)

Ethyl 3-(1-naphthylmethyl)-2,4,5-trioxoimidazolidine-1-acetate [Compound 9].
Melting point: 172.0°–175.0° C.
IR(KBr): 1747(C=O), 1734(C=O), 1446, 1232, 1151, 797, 575 $cm^{-1}$
$^1$H-NMR(DMSO-$d_6$): 1.19(t,J=7.0Hz,3H,$CH_3$), 4.15(q,J=7.0Hz,2H, O-$CH_2$), 4.43(s,2H,N—$CH_2$—$CO_2$), 5.22(s, 2H,$CH_2$—N), 7.45–7.64 (m,4H,Ar), 7.91(d,J=8.6Hz,1H, Ar), 7.98(d,J=8.6Hz,1H,Ar), 8.19 (d,J=8.6Hz,1H,Ar)

Ethyl 3-(2-naphthylmethyl)-2,4,5-trioxoimidazolidine-1-acetate [Compound 10].
Melting point: 149.0°–150.0° C.
IR(KBr): 1734(C=O), 1446, 1238, 1149, 766 $cm^{-1}$
$^1$H-NMR(DMSO-$d_6$): 1.19 (t,J=7.0Hz, 3H, $CH_3$), 4.16(q,J=7.0Hz, 2H, O-$CH_2$), 4.43(s,2H,N—$CH_2$—$CO_2$), 4.92(s, 2H,$CH_2$—N), 7.47(dd,J=8.5,1.8Hz,1H,Ar), 7.52(s,1H, Ar), 7.52(dd,J=9.5,1.8Hz,1H,Ar), 7.86–7.95(m,4H,Ar)

Ethyl 3-[2-(9,10-anthraquinonyl)methyl]-2,4,5-trioxoimidazolidine-1-acetate [Compound 11].
Melting point: 217.0°–218.0° C.
IR(KBr): 1731(C=O), 1674, 1446, 1298, 1147 $cm^{-1}$
$^1$H-NMR(DMSO-$d_6$): 1.21(t,J=7.0Hz,3H,$CH_3$), 4.17(q,J=7.0Hz,2H, O-$CH_2$), 4.43(s,2H,N—$CH_2$—$CO_2$), 4.98(s, 2H,$CH_2$—N), 7.88–7.98(m,3H,Ar), 8.18–8.24(m,H,Ar)

Ethyl 3-(2-benzothiazolylmethyl)-2,4,5-trioxoimidazolidine-1-acetate [Compound 12]
Melting point: 151.5°–153.0° C.
IR(KBr): 1734(C=O), 1446, 1221, 1147, 770 $cm^{-1}$
$^1$H-NMR(DMSO-$d_6$): 1.21(t,J=7.0Hz,3H,$CH_3$), 4.17(q,J=7.0Hz,2H, O-$CH_2$), 4.47(s,2H,N—$CH_2$—$CO_2$), 5.25(s, 2H,$CH_2$—N), 7.46 (ddd,J=7.7,7.7,1.2Hz,1H,Ar), 7.53 (ddd,J=7.7,7.7,1.2Hz,1H,Ar), 7.99(dd,J=7.7,1.2Hz,1H, Ar), 8.11(dd,J=7.7,1.2Hz,1H,Ar)

Ethyl 3-(N-phthalimidemethyl)-2,4,5-trioxoimidazolidine-1-acetate [Compound 13].

Melting point: 197.0°–199.0° C.
IR(KBr): 1743(C=O), 1406, 1336, 1221, 1141, 762, 723 cm$^{-1}$
$^1$H-NMR(DMSO-d$_6$): 1.19(t,J=7.0Hz,3H,CH$_3$), 4.15(q,J=7.0Hz,2H, O-CH$_2$), 4.38(s,2H,N—CH$_2$—CO$_2$), 5.39(s, 2H,CH$_2$—N), 7.82–7.96(m,4H,Ar)

Ethyl 3- [1-(2-bromonaphthyl) methyl]-2,4,5-trioxoimidazolidine-1-acetate [Compound 14].
Melting point: 184.5°–185.5° C.
IR(KBr): 1736(C=O), 1446, 1227, 1153, 771 cm$^{-1}$
$^1$H-NMR(DMSO-d$_6$): 1.21(t,J=7.0Hz,3H,CH$_3$), 4.17(q,J=7.0Hz,2H, O-CH$_2$), 4.44(s,2H,N—CH$_2$—CO$_2$), 5.04(s, 2H,CH$_2$—N), 7.56(d,J=8.5Hz,1H,Ar), 7.64(dd, J=7.0, 7.0Hz,1H,Ar), 7.72 (dd, J=8.5,7.0Hz,1H,Ar), 7.95–8.05 (m, 2H,Ar), 8.25 (d,J=8.5Hz,1H,Ar)

Ethyl 3- [2-(6-nitrobenzothiazolyl) methyl]-2,4,5-trioxoimidazolidine-1-acetate [Compound 15].
Melting point: 183.0°–184.0° C.
IR(KBr): 1743(C=O), 1738(C=O), 1524(NO$_2$), 1444, 1346(NO$_2$), 1225 cm$^{-1}$
$^1$H-NMR(DMSO-d$_6$): 1.21(t,J=7.1Hz,3H,CH$_3$), 4.18(q,J=7.1Hz,2H, O-CH$_2$), 4.48 (s,2H,N—CH$_2$—CO$_2$), 5.34(s, 2H,CH$_2$—Ar), 8.19(d,J=9.0Hz,1H,Ar), 8.34(dd,J=9.0, 2.4Hz,1H,Ar), 9.22 (d,J=2.4Hz,1H,Ar)

Ethyl 3- [2-(6-methylbenzothiazolyl)methyl]-2,4,5-trioxoimidazolidine-1-acetate [Compound 16].
Melting point: 155.0°–156.0° C.
IR(KBr): 1738(C=O), 1443, 1402, 1234, 1147 cm$^{-1}$
$^1$H-NMR (DMSO-d$_6$): 1.21(t, J=7.1Hz, 3H, CH$_3$), 2.44(s, 3H, CH$_3$), 4.18(q,J=7.1Hz,2H,O-CH$_2$), 4.47(s,2H,N—CH$_2$—CO$_2$), 5.21(s,2H,CH$_2$—Ar), 7.34(d,J=8.2Hz,1H, Ar), 7.86(d,J=8.2Hz,1H,Ar), 7.90(s,1H,Ar)

Ethyl 3-[2-(5-chlorobenzothiazolyl)methyl]-2,4,5-trioxoimidazolidine-1-acetate [Compound 17].
Melting point: 163.0°–163.5° C.
IR(KBr): 1749(C=O), 1734(C=O), 1441, 1226, 1152, 816 cm$^{-1}$
$^1$H-NMR(DMSO-d$_6$): 1.21(t,J=7.1Hz,3H,CH$_3$), 4.18(q,J=7.1Hz,2H, O-CH$_2$), 4.47(s,2H,N—CH$_2$—CO$_2$), 5.26 (s,2H, CH$_2$—Ar), 7.53 (dd,J=8.5,1.9Hz,1H,Ar), 8.09 (d,J=1.9Hz, 1H,Ar), 8.17 (d,J=8.5Hz,1H,Ar)

Ethyl 3- [2-(6-chlorobenzothiazolyl)methyl]-2,4,5-trioxoimidazolidine-1-acetate [Compound 18].
Melting point: 181.0°–182.5° C.
IR(KBr): 1734(C=O), 1444, 1405, 1240, 1148, 815 cm$^{-1}$
$^1$H-NMR(DMSO-d$_6$): 1.21(t,J=7.1Hz,3H,CH$_3$), 4.17(q,J=7.1Hz,2H, O-CH$_2$), 4.47(s,2H,N—CH$_2$—CO$_2$), 5.25(s, 2H,CH$_2$—Ar), 7.56(dd,J=8.8,2.2Hz,1H,Ar), 7.99(d,J=8.8Hz,1H,Ar), 8.29(d,J=2.2Hz,1H,Ar)

Ethyl 3- [2-(4-chlorobenzothiazolyl)methyl]-2,4,5-trioxoimidazolidine-1-acetate [Compound 19].
Melting point: 186.5°–187.5° C.
IR(KBr): 1735(C=O), 1729(C=O), 1444, 1403, 1240, 1147, 1102, 780, 743 cm$^{-1}$
$^1$H-NMR(DMSO-d$_6$): 1.21(t,J=7.0Hz,3H,CH$_3$), 4.17(q,J=7.0Hz,2H, O-CH$_2$), 4.46(s,2H,N—CH$_2$—CO$_2$), 5.28 (s,2H, CH$_2$—Ar), 7.47(dd,J=8.0,8.0Hz,1H,Ar), 7.64(d,J=8.0Hz,1H,Ar), 8.11(d, J=8.0Hz, 1H, Ar)

Ethyl 3-[2-(6-fluorobenzothiazolyl)methyl]-2,4,5-trioxoimidazolidine-1-acetate [Compound 20].
Melting point: 154.0°–155.0° C.
IR(KBr): 1734(C=O), 1447, 1228, 1149, 770 cm$^{-1}$
$^1$H-NMR(DMSO-d$_6$): 1.21(t,J=7.1Hz,3H, CH$_3$), 4.17 (q,J=7.1Hz,2H, O-CH$_2$), 4.46(s,2H,N—CH$_2$—CO$_2$), 5.23 (s,2H,CH$_2$—Ar), 7.39(ddd,J=9.2,9.2,2.5Hz,1H,Ar), 8.01 (dd,J=9.2,5.0Hz,1H,Ar), 8.04 (dd, J=9.2,2.5Hz,1H,Ar)

Ethyl 3-[2-(6-methoxybenzothiazolyl)methyl]-2,4,5-trioxoimidazolidine-1-acetate [Compound 21].

Melting point: 150.5°–152.0° C.
IR(KBr): 1736(C=O), 1443, 1259, 1227, 1146, 825 cm$^{-1}$
$^1$H-NMR(DMSO-d$_6$): 1.21(t,J=7.1Hz,3H,CH$_3$), 3.83(s,3H, O-CH$_3$), 4.17(q,J=7.1Hz,2H,O-CH$_2$), 4.46(s,2H,N—CH$_2$CO$_2$), 5.18(s,2H,CH$_2$—Ar), 7.11(dd,J=9.0,2.6Hz, 1H,Ar), 7.68(d,J=2.6Hz,1H,Ar), 7.86 (d, J=9.0Hz, 1H,Ar)

Ethyl 3- [2-(5-bromobenzothiazolyl) methyl]-2,4,5-trioxoimidazolidine-1-acetate [Compound 22].
Melting point: 157.0°–158.0° C. (decomp.)
IR(KBr): 1751(C=O), 1732(C=O), 1444, 1430 cm$^{-1}$
$^1$H-NMR(DMSO-d$_6$): 1.21(t,J=7.0Hz,3H,CH$_3$), 4.18(q,J=7.0Hz,2H, O-CH$_2$), 4.47(s,2H,N—CH$_2$—CO), 5.26(s, 2H,CH$_2$—Ar), 7.64(dd,J=8.6,1.8Hz,1H,Ar—H), 8.11(d, J=8.6Hz,1H,Ar—H), 8.22(d,J=1.8Hz, 1H,Ar—H)

Ethyl 3-(2-trifluoromethylbenzyl)-2,4,5-trioxoimidazolidine-1-acetate [Compound 23].
Melting point: 173.5°–174.5° C.
MS m/z: 358 (M$^+$)
IR(KBr): 1735(C=O), 1455, 1320, 1225, 1105 cm$^{-1}$
$^1$H-NMR(DMSO-d$_6$): 1.22(t,J=7.0Hz,3H,CH$_3$), 4.17(q,J=7.0Hz,2H, O-CH$_2$), 4.44(s,2H,N—CH$_2$—CO$_2$), 4.89(s, 2H,CH$_2$—N), 7.54 (dd,J=8.0,7.0Hz,1H,Ar—H), 7.59(d, J=8.0Hz,1H,Ar—H), 7.66(dd,J=8.0,7.0Hz,1H,Ar—H), 7.78(d,J=8.0Hz,1H,Ar—H)

Ethyl 3-(3-trifluoromethylbenzyl)-2,4,5-trioxoimidazolidine-1-acetate [Compound 24].
Melting point: 109.5°–110.5° C.
MS m/z: 358 (M$^+$)
IR(KBr): 1730(C=O), 1455, 1439, 1335, 1215 cm$^{-1}$
$^1$H-NMR(DMSO-d$_6$): 1.20(t,J=7.0Hz,3H,CH$_3$), 4.16(q,J=7.0Hz,2H, O-CH$_2$), 4.41(s,2H,N—CH$_2$—CO$_2$), 4.86(s, 2H,CH$_2$—N), 7.60(dd,J=7.5,7.5Hz,1H,Ar—H), 7.64–7.71(m,2H,Ar—H), 7.74(s,1H, Ar—H)

Ethyl 3-(4-trifluoromethylbenzyl)-2,4,5-trioxoimidazolidine-1-acetate [Compound 25].
Melting point: 138.0°–139.5° C.
Ms m/z: 358 (M$^+$)
IR(KBr): 2995, 1750(C=O), 1725(C=O), 1450, 1320, 1240, 1120, 775 cm$^{-1}$
$^1$H-NMR (DMSO-d$_6$): 1.20 (t, J=7.0Hz, 3H, CH$_3$), 4.16 (q, J=7.0Hz, 2H, O-CH$_2$), 4.41(s,2H,N—CH$_2$—CO$_2$), 4.85 (s,2H,CH$_2$—N), 7.59 (d, J=8.0Hz, 2H,Ar—H), 7.74 (d, J=8.0Hz, 2H,Ar—H)

Benzyl 3-(3-cyanobenzyl)-2,4,5-trioxoimidazolidine-1-acetate [Compound 26].
Melting point: 148.5°–149.0° C.
IR(KBr): 2235(CN), 1734 (C=O), 1446, 1431, 1209, 758 cm$^{-1}$
$^1$H-NMR (DMSO-d$_6$): 4.50(s, 2H, N—CH$_2$—CO$_2$), 4.82(s, 2H, CH$_2$—N), 5.20(s,2H,O-CH$_2$), 7.33–7.43(m,5H,Ar—H), 7.57(dd, J=7.9,7.9Hz,1H, Ar—H), 7.70(d,J=7.9Hz, 1H, Ar—H), 7.78(d,J=7.9Hz,1H,Ar—H), 7.87(s,1H,Ar—H)

Benzyl 3-(4-cyanobenzyl)-2,4,5-trioxoimidazolidine-1-acetate [Compound 27].
Melting point: 120.5°–121.0 ° C.
IR(KBr): 2190(CN), 1705(C=O), 1420, 1400, 1195, 740 cm$^{-1}$
$^1$H-NMR(DMSO-d$_6$): 4.49(s,2H,N—CH$_2$—CO$_2$), 4.84(s, 2H, CH$_2$—N), 5.20 (s,2H—O—CH$_2$), 7.30–7.40(m,5H, O—C—Ar), 7.55(d,J=8.0Hz, 2H, Ar—H), 7.82(d,J=8.0Hz,2H,Ar—H)

Ethyl 3-(3-methoxycarbonylbenzyl)-2,4,5-trioxoimidazolidine-1-acetate [Compound 28].
Melting point: 121.0°–122.0° C.
MS m/z: 348 (M$^+$)
IR(KBr): 1735(C=O), 1445, 1425, 1400, 1255, 1145, 755 cm$^{-1}$ $^1$H-NMR(DMSO-d$_6$): 1.19(t,J=7.0Hz,3H,C—CH$_3$), 3.86(s, 3H,O—CH$_3$), 4.16(q,J=7.0Hz,2H,O—CH$_2$), 4.39(s,2H, N—CH$_2$—CO$_2$), 4.82(s,2H, CH$_2$—N), 7.52(dd,J=7.5, 7.5Hz,1H,Ar—H), 7.63(d,J=7.5Hz,1H,Ar—H), 7.90 (d,J=7.5Hz, 1H,Ar—H), 7.95(s,1H,Ar—H)

Ethyl 3-(3-carbamoylbenzyl)-2,4,5-trioxoimidazolidine-1-acetate [Compound 29].

Melting point: 190.5°–192.5° C.

MS m/z: 333 (M$^+$)

IR(KBr): 3450(NH$_2$), 1730(C=O), 1645, 1450, 1430, 1395, 1240 cm$^{-1}$ $^1$H-NMR(DMSO-d$_6$): 1.19(t,J=7.0Hz,3H,CH$_3$), 4.16(q,J=7.0Hz,2H, O-CH$_2$), 4.41(s,2H,N—CH$_2$—CO$_2$), 4.79(s, 2H,CH$_2$—N), 7.30–7.58(m,3H,Ar—H), 7.75(brs,2H, NH$_2$), 8.03(s,1H,Ar—H)

Benzyl 3-(3-methoxycarbonylbenzyl)-2,4,5-trioxoimidazolidine-1-acetate [Compound 30].

Melting point: 105.0°–107.0° C. (decomp.)

IR(KBr): 1734(C=O), 1448, 1429, 1288, 1207 cm$^{-1}$ $^1$H-NMR (DMSO-d$_6$): 3.86(s,3H, O—CH$_3$), 4.49(s,2H, N—CH$_2$—CO$_2$), 4.82(s,2H,CH$_2$—N), 5.19(s,2H,O—CH$_2$), 7.30–7.40(m,5H,O—C—Ar), 7.51(dd,J=7.5, 7.5Hz,1H,Ar—H), 7.62(d,J=7.5Hz,2H,Ar—H), 7.90 (d,J=7.5Hz,1H,Ar—H), 7.96(s,1H,Ar—H)

Ethyl 3-(4-chloro-3-nitrobenzyl)-2,4,5-trioxoimidazolidine-1-acetate [Compound 31].

Melting point: 141.0°–144.0° C. (decomp.)

MS m/z: 369 (M$^+$)

IR(KBr): 1735(C=O), 1535(NO$_2$), 1450, 1230 cm$^{-1}$ $^1$H-NMR(DMSO-d$_6$): 1.20(t,J=7.0Hz,3H,CH$_3$), 4.16(q,J=7.0Hz,2H, O-CH$_2$), 4.40(s,2H,N—CH$_2$—CO$_2$), 4.86(s, 2H,CH$_2$—N), 7.70(dd,J=8.0,1.5Hz,1H,Ar), 7.78(d,J=8.0Hz,1H,Ar—H), 8.08(d,J=1.5Hz,1H,Ar—H)

EXAMPLE 3

The Compound 1 (2.1 g) of Example 1 was added to a mixed solution of 6 mL of acetic acid and 2 mL of concentrated hydrochloric acid, the mixture was heated to reflux for two hours, concentrated in vacuo, then 6 mL of acetic acid and 2 mL of concentrated hydrochloric acid were added thereto and the mixture was heated to reflux for one hour. Water was added to the residue obtained by concentrating the reaction mixture and the resulting precipitate was collected by filtration, washed with water, dried and recrystallized from ethanol to give 3-[2-(5-trifluoromethylbenzothiazolyl)-methyl]-2,4,5-trioxoimidazolidine-1-acetic acid [Compound 32].

Melting point: 211.0°–212.0° C.

MS(EI,70eV): 387(M$^+$,72), 258(43), 230(12), 216(19), 203(80), 56(100)

IR(KBr): 2926(OH), 1741(C=O), 1443, 1421, 1333, 1149, 1122 cm$^{-1}$ $^1$H-NMR(DMSO-d$_6$): 4.36(s,2H,N—CH$_2$—CO$_2$), 5.32 (s,2H, CH$_2$—Ar), 7.80(d,J=8.4Hz,1H,Ar), 8.37(s,1H,Ar), 8.39(d,J=8.4Hz,1H,Ar), 13.47 (brs, 1H,OH)

Elementary analysis (C$_{14}$H$_8$F$_3$N$_3$O$_5$S 0.1H$_2$O): Calculated (C=43.22,H=2.12,N=10.80), Found (C=43.60,H=2.53,N=10.97)

EXAMPLE 4

Reactions similar to the synthesis of Compound 32 of Example 3 were carried out to give the following compounds:

3-(3-pyridylmethyl)-2,4,5-trioxoimidazolidine-1-acetic acid [Compound 33].

Melting point: 208.5°–210.0° C. (decomp.)

IR(KBr): 3000(OH), 1735(C=O), 1705(C=O), 1605, 1435, 1255, 1140, 755 cm$^{-1}$ $^1$H-NMR(DMSO-d$_6$): 4.29(s,2H,N—CH$_2$—CO$_2$), 4.82 (s,2H, CH$_2$—N), 7.49 (dd, J=7.5,5.0Hz,1H,Ar), 7.75(d, J=7.5Hz,1H, Ar), 8.57(d,J=5.0Hz,1H,Ar), 8.63(s,1H,Ar), 13.16(brs,1H,OH)

Elementary analysis (C$_{11}$H$_9$N$_3$O$_5$): Calculated (C=50.20,H=3.45,N=15.96), Found (C=50.12,H=3.59,N=15.80)

3-(4-pyridylmethyl)-2,4,5-trioxoimidazolidine-1-acetic acid [Compound 34].

Melting point: 251.0°–252.0° C. (decomp.)

IR(KBr): 3000(OH), 1740(C=O), 1435, 1400, 1245, 1140, 755 cm$^{-1}$ $^1$H-NMR(DMSO-d$_6$): 4.31(s,2H,N—CH$_2$—CO$_2$), 4.80(s, 2H,CH$_2$—N), 7.37(d,J=5.5Hz,2H,Ar), 8.54(d,J=5.5Hz, 2H,Ar), 13.30(brs,1H,OH)

Elementary analysis (C$_{11}$H$_9$N$_3$O$_5$): Calculated (C=50.20,H=3.45,N=15.96), Found (C=50.11,H=3.43,N=15.88)

3-(2-thienylmethyl)-2,4,5-trioxoimidazolidine-1-acetic acid [Compound 35].

Melting point: 205.5°–210.0° C. (decomp.)

IR(KBr): 3000(OH), 1730(C=O), 1590, 1440 cm$^{-1}$ $^1$H-NMR(DMSO-d$_6$): 4.30(s,2H,N—CH$_2$—CO$_2$), 4.90(s, 2H,CH$_2$—N), 7.01(dd,J=5.0,3.5Hz,1H,Ar), 7.12(d,J=3.5Hz,1H,Ar), 7.50 (d,J=5.0Hz,1H,Ar)

3-[3-(5-bromopyridyl)methyl]-2,4,5-trioxoimidazolidine-1-acetic acid [Compound 36].

Melting point: 221.0°–222.0° C.

IR(KBr): 3000(OH), 1734(C=O), 1448, 1138, 771 cm$^{-1}$ $^1$H-NMR(DMSO-d$_6$): 4.29(s,2H,N—CH$_2$—CO$_2$), 4.82(s, 2H,CH$_2$—N), 8.06(s,1H,Ar), 8.58(s,1H,Ar), 8.65(s,1H, Ar), 13.41(brs,1H,OH)

Elementary analysis (C$_{11}$H$_8$BrN$_3$O$_5$): Calculated (C=38.62, H=2.36,N=12.28), Found (C=38.52,H=2.41,N=12.19)

3-[3-(2-chloropyridyl)methyl]-2,4,5-trioxoimidazolidine-1-acetic acid [Compound 37].

Melting point: 234.5°–236.0° C.

IR(KBr): 3000(OH), 1740(C=O), 1722(C=O), 1437, 1236, 1151, 754 cm$^{-1}$ $^1$H-NMR(DMSO-d$_6$): 4.31(s,2H,N—CH$_2$—CO$_2$), 4.82(s, 2H,CH$_2$—N), 7.45(dd,J=8.0,5.0Hz,1H,Ar), 7.96(d,J=8.0Hz,1H,Ar), 8.38 (d,J=5.0Hz, 1H,Ar), 13.42 (brs, 1H,OH)

MS m/z: 297 (M$^+$)

Elementary analysis (C$_{11}$H$_8$ClN$_3$O$_5$): Calculated (C=44.39, H=2.71,N=14.12), Found (C=44.44,H=2.71,N=14.10)

3-[3-(6-chloropyridyl)methyl]-2,4,5-trioxoimidazolidine-1-acetic acid [Compound 38].

Melting point: 202.0°–203.5° C.

IR(KBr): 3100(OH), 1738(C=O), 1718(C=O), 1601, 1450, 1390, 760 cm$^{-1}$ $^1$H-NMR(DMSO-d$_6$): 4.29(s,2H,N—CH$_2$—CO$_2$), 4.81(s, 2H,CH$_2$—N), 7.53(d,J=8.2Hz,1H,Ar), 7.84(dd,J=8.2, 1.7Hz,1H,Ar), 8.42(d,J=2.5Hz,1H,Ar), 13.37(brs, 1H,OH)

Elementary analysis (C$_{11}$H$_8$ClN$_3$O$_5$): Calculated (C=44.39, H=2.71,N=14.12), Found (C=44.68,H=2.93,N=14.12)

3-(2-pyridylmethyl)-2,4,5-trioxoimidazolidine-1-acetic acid [Compound 39].

Melting point: 251.0°–253.0° C. (decomp.)

IR(KBr): 3000(OH), 1737(C=O), 1450, 1249, 1159, 775 cm$^{-1}$ $^1$H-NMR(DMSO-d$_6$): 4.33(s,2H,N—CH$_2$—CO$_2$), 4.88(s, 2H,CH$_2$—N), 7.32(dd,J=7.5,3.5Hz,1H,Ar), 7.45(d,J=7.5Hz,1H,Ar), 7.80(dd,J=7.5,7.5Hz,1H,Ar), 8.50(d,J=3.5Hz,1H,Ar), 13.43(brs,1H,OH)

MS m/z: 363 (M$^+$)

Elementary analysis ($C_{11}H_9N_3O_5$): Calculated (C=50.20,H=3.45,N=15.96), Found (C=49.92,H=3.37,N=16.08)

3-(1-naphthylmethyl)-2,4,5-trioxoimidazolidine-1-acetic acid [Compound 40].

Melting point: 225.0°–228.0° C.

IR(KBr): 3000(OH), 1738(C=O), 1722(C=O), 1444, 1400, 1246, 1151, 798 cm$^{-1}$ $^1$H-NMR(DMSO-d$_6$): 4.34(s,2H,N—CH$_2$—CO$_2$), 5.21(s, 2H,CH$_2$—N), 7.34–7.64(m,4H,Ar), 7.90(d,J=7.9Hz,1H, Ar), 7.98(d,J=7.9Hz,1H,Ar), 8.20(d,J=7.9Hz,1H,Ar), 13.42(brs,1H,OH)

Elementary analysis ($C_{16}H_{12}N_2O_5$): Calculated (C=61.54, H=3.87,N=8.97), Found (C=61.28,H=3.94,N=8.89)

3-(2-naphthylmethyl)-2,4,5-trioxoimidazolidine-1-acetic acid [Compound 41].

Melting point: 192.5°–194.0° C.

IR(KBr): 3000(OH), 1768(C=O), 738(C=O), 1716 (C=O), 1441, 1402, 1250, 1149, 762 cm$^{-1}$ $^1$H-NMR(DMSO-d$_6$): 4.42(s,2H,N—CH$_2$—CO$_2$), 4.92(s, 2H,CH$_2$—N), 7.47 (dd, J=8.9,2.0Hz, 1H,Ar), 7.52(s,1H, Ar), 7.52 (dd,J=9.4,2.0Hz, 1H,Ar), 7.86–7.94(m,4H,Ar), 13.46 (brs, 1H, OH)

MS m/z: 312 (M$^+$)

Elementary analysis ($C_{16}H_{12}N_2O_5$): Calculated (C=61.54, H=3.87,N=8.97), Found (C=61.24,H=4.04,N=8.76)

3-[2-(9,10-anthraquinonyl)methyl]-2,4,5-trioxoimidazolidine-1-acetic acid [Compound 42].

Melting point: 236.5°–238.5° C.

IR(KBr): 3100(OH), 1736(C=O), 1674, 1446, 1300, 1149, 711 cm$^{-1}$ $^1$H-NMR(DMSO-d$_6$): 4.32(s, 2H,N—CH$_2$—CO$_2$), 4.98(s, 2H, CH$_2$—N), 7.86–7.99(m,3H,Ar), 8.13–8.27(m,H,Ar), 13.41(brs,1H,OH)

Elementary analysis ($C_{20}H_{12}N_2O_7$ · 0.5H$_2$O): Calculated (C=59.86,H=3.27,N=6.98), Found (C=59.91,H=3.42,N=6.82)

3-(2-benzothiazolylmethyl)-2,4,5-trioxoimidazolidine-1-acetic acid [Compound 43].

Melting point: 264.0°–265.0° C. (decomp.)

IR(KBr): 3100(OH), 1736(C=O), 1443, 1402, 1215, 1149, 763 cm$^{-1}$ $^1$H-NMR(DMSO-d$_6$): 4.38(s,2H,N—CH$_2$—CO$_2$), 5.25(s, 2H,CH$_2$—N), 7.46 (dd,J=7.4,7.4Hz, 1H,Ar), 7.52 (dd,J= 7.4,7.4Hz, 1H,Ar), 7.99(d,J=7.4Hz,1H,Ar), 8.12(d,J= 7.4Hz,1H,Ar), 13.43(brs,1H,OH)

MS m/z: aaa(M$^+$)

Elementary analysis ($C_{13}H_9N_3O_5S$): Calculated (C=48.90, H=2.84,N=13.16), Found (C=48.92,H=2.90,N=13.06)

3-(N-phthalimidemethyl)-2,4,5-trioxoimidazolidine-1-acetic acid [Compound 44].

Melting point: 266.0°–268.0° C. (decomp.)

IR(KBr): 3000(OH), 1740(C=O), 1412, 1331, 1169, 926, 731 590 cm$^{-1}$ $^1$H-NMR(DMSO-d$_6$): 4.28(s,2H,N—CH$_2$—CO$_2$), 5.39(s, 2H,CH$_2$—N), 7.85–7.95(m,4H,Ar), 13.41(brs,1H,OH)

MS m/z: 331(M$^+$)

Elementary analysis ($C_{14}H_9N_3O_7$): Calculated (C=50.77,H=2.74,N=12.69), Found (C=50.65,H=2.82,N=12.72)

3-[1-(2-bromonaphthyl)methyl]-2,4,5-trioxoimidazolidine-1-acetic acid [Compound 45].

Melting point: 205.0°–210.0° C. (decomp.)

IR(KBr): 3000 (OH), 1738 (C=O), 1720(C=O), 1433, 1153, 760 cm$^{-1}$ $^1$H-NMR(DMSO-d$_6$): 4.33 (s,2H,N—CH$_2$—CO$_2$), 5.04 (s,2H,CH$_2$—N), 7.55(d,J=8.9Hz,1H,Ar), 7.64(dd,J=8.1, 7.4Hz,1H,Ar), 7.72 (dd, J=8.1,7.4Hz, 1H,Ar), 7.98 (d,J= 8.1Hz, 1H,Ar), 8.00(d,J=8.1Hz,1H,Ar), 8.25(d,J=8.9Hz, 1H,Ar), 13.46(brs,1H,OH)

MS m/z: 392(M$^+$($^{81}$Br)), 392(M$^+$($^{79}$Br))

Elementary analysis ($C_{16}H_{11}BrN_2O_5$): Calculated (C=49.13,H=2.83,N=7.16), Found (C=48.89,H=2.97,N=6.98)

3-[2-(6-nitrobenzothiazolyl)methyl]-2,4,5-trioxoimidazolidine-1-acetic acid [Compound 46].

Melting point: 130.0°–131.0° C. (decomp.)

MS(EI,70eV): 364(M$^+$,79), 235(44), 207(11), 180(47), 56(100)

IR(KBr): 3000(OH), 1745(C=O), 1734(C=O), 1525 (NO$_2$), 1435, 1344 (NO$_2$) cm$^{-1}$ $^1$H-NMR(DMSO-d$_6$): 4.36(s,2H,N—CH$_2$—CO$_2$), 5.34(s, 2H,CH$_2$—Ar), 8.19 (d,J=9.0Hz, 1H,Ar), 8.34 (dd, J=9.0, 2.3Hz, 1H,Ar), 9.21 (d,J=2.3Hz, 1H,Ar), 13.47 (brs, 1H, OH)

Elementary analysis ($C_{13}H_8N_4O_7S$): Calculated (C=42.86, H=2.21,N=15.38), Found (C=42.90,H=2.33,N=15.15)

3-[2-(6-methylbenzothiazolyl)methyl]-2,4,5-trioxoimidazolidine-1-acetic acid [Compound 47].

Melting point: 277.0°–278.0° C.

MS(EI,70eV): 333(M$^+$, 100), 204(50), 176 (24), 162 (26), 149 (86), 56(63)

IR(KBr): 3000(OH), 1738(C=O), 1441, 1402, 1213, 1151, 764 cm$^{-1}$ $^1$H-NMR(DMSO-d$_6$): 2.44 (s,3H,CH$_3$), 4.35(s,2H,N—CH$_2$CO$_2$), 5.21 (s, 2H, CH$_2$—Ar), 7.34 (d,J=8.3Hz, 1H,Ar), 7.86(d,J=8.3Hz,1H,Ar), 7.89(s,1H,Ar), 13.47 (brs,1H,OH)

Elementary analysis ($C_{14}H_{11}N_3O_5S$): Calculated (C=50.45 ,H=3.33 ,N=12.61), Found (C=50.39, H=3.30 ,N=12.66)

3-[2-(5-chlorobenzothiazolyl)methyl]-2,4,5-trioxoimidazolidine-1-acetic acid [Compound 48].

Melting point: 265.0°–268.0° C. (decomp.)

MS(EI,70eV): 355(M$^+$($^{37}$Cl),21), 353(M$^+$($^{35}$Cl),59), 224 (44), 196(20), 182(19), 169(64), 56(100)

IR(KBr): 3006(OH), 1782(C=O), 1741(C=O), 1429, 1351, 1213, 1120, 886, 799, 758 cm$^{-1}$ $^1$H-NMR(DMSO-d$_6$): 4.36(s,2H,N—CH$_2$—CO$_2$), 5.26(s, 2H,CH$_2$—Ar), 7.52 (dd,J=8.6,2.0Hz,1H,Ar), 8.10(d,J= 2.0Hz,1H,Ar), 8.16 (d,J=8.6Hz, 1H,Ar), 13.45 (brs, 1H,OH)

Elementary analysis ($C_{13}H_8ClN_3O_5S$): Calculated (C=44.14,H=2.28,N=11.88), Found (C=44.20,H=2.46,N=11.80)

3-[2-(6-chlorobenzothiazolyl)methyl]-2,4,5-trioxoimidazolidine-1-acetic acid [Compound 49].

Melting point: 265.0°–266.0° C.

MS(EI,70eV): 355(M$^+$($^{37}$Cl),32), 353(M$^+$($^{35}$Cl),59), 226 (20), 224(52), 196(23), 82(25), 171(28), 169(76), 56(100)

IR(KBr): 3000(OH), 1746(C=O), 1734(C=O), 1435, 1398, 1345, 1143, 1117, 757 cm$^{-1}$ $^1$H-NMR(DMSO-d$_6$): 4.36(s,2H,N—CH$_2$—CO$_2$), 5.25(s, 2H,CH$_2$—Ar), 7.56(d,J=8.7Hz,1H,Ar), 7.99(d,J=8.7Hz, 1H,Ar), 8.29(s,1H,Ar), 13.45 (brs, 1H,OH)

Elementary analysis ($C_{13}H_8ClN_3O_5S$): Calculated (C=44.14,H=2.28,N=11.88), Found (C=43.98,H=2.27,N=11.89)

3-[2-(4-chlorobenzothiazolyl)methyl]-2,4,5-trioxoimidazolidine-1-acetic acid [Compound 50].

Melting point: 238.0°–240.0° C.

MS(EI,70eV): 355(M$^+$($^{37}$Cl),32), 353(M$^+$(35Cl),82), 226 (16), 224(41), 196(17), 182(17), 171(24), 169(64), 56(100) IR(KBr): 2900(OH), 1732(C=O), 1442, 1401, 1201, 1146, 778, 762, 607 cm$^{-1}$ $^1$H-NMR(DMSO-d$_6$): 4.35 (s, 2H,N—CH$_2$—CO$_2$), 5.27 (s, 2H, CH$_2$—Ar), 7.47 (dd,J=8.0,8.0Hz, 1H,Ar), 7.63 (d,J= 8.0Hz, 1H,Ar), 8.11(d,J=8.0Hz,1H,Ar), 13.41(brs,1H, OH)

Elementary analysis ($C_{13}H_8ClN_3O_5S$): Calculated (C=44.14,H=2.28, N=11.88), Found (C=44.32, H=2.47, N=11.56)

3-[2-(6-fluorobenzothiazolyl)methyl]-2,4,5-trioxoimidazolidine-1-acetic acid [Compound 51].
Melting point: 261.0°–262.0° C.
MS(EI,70eV): 337($M^+$,72), 208(57), 180(30), 166(34), 153 (100)
IR(KBr): 2900(OH), 1744(C=O), 1721(C=O), 1521, 1439, 1406, 1204, 1154, 1116, 769, 631 $cm^{-1}$
$^1$H-NMR(DMSO-$d_6$): 4.34(s,2H,N—$CH_2$—$CO_2$), 5.22 (s,2H,$CH_2$—Ar), 7.34–7.41(m, 1H,Ar), 7.97–8.06(m,2H, Ar), 13.43(brs,1H,OH)
Elementary analysis ($C_{13}H_8FN_3O_5S$): Calculated (C=46.29, H=2.39,N=12.46), Found (C=46.59,H=2.59,N=12.68)

3-[2-(6-methoxybenzothiazolyl)methyl]-2,4,5-trioxoimidazolidine-1-acetic acid [Compound 52].
Melting point: 270.0°–271.0° C.
MS(EI,70eV): 349($M^+$, 100),220(47), 192(28), 178(28), 165 (74), 56(53)
IR(KBr): 3000(OH), 1734(C=O), 1443, 1421, 1223, 1149 $cm^{-1}$
$^1$H-NMR(DMSO-$d_6$): 3.83(s, 3H,O—$CH_3$), 4.34(s, 2H,N—$CH_2$—$CO_2$), 5.18 (s, 2H, $CH_2$—Ar), 7.11(dd, J=8.9, 2.4Hz, 1H, Ar), 7.67 (d,J=2.4Hz, 1H,Ar), 7.87 (d,J=8.9Hz, 1H,Ar)
Elementary analysis ($C_{14}H_{11}N_3O_6$ 0.1$H_2O$): Calculated (C=47.89,H=3.22,N=12.97), Found (C=47.87,H=3.10,N=11.53)

3-[2-(5-bromobenzothiazolyl)methyl]-2,4,5-trioxoimidazolidine-1-acetic acid [Compound 53].
Melting point: 272.0°–273.0° C. (decomp.)
MS(EI,70eV) m/z: 293($M^+$,10), 275(4), 157 (100), 136(36), 120(28), 90(54), 74(47), 56(43)
IR(KBr): 3000(OH), 1740(C=O), 1428, 1400, 1211 $cm^{-1}$
$^1$H-NMR(DMSO-$d_6$): 4.34(s, 2H,N—$CH_2$—CO), 5.26 (s, 2H,$CH_2$—Ar), 7.64 (dd, J=8.6,1.6Hz, 1H, Ar—H), 8.11 (d, J=8.6Hz, 1H, Ar—H), 8.23 (d,J=1.6Hz, 1H,Ar—H), 13.20 (brs, 1H, COOH)
Elementary analysis ($C_{13}H_8BrN_3O_5S$): Calculated (C=39.21,H=2.03,N=10.55), Found (C=39.41,H=1.86,N=10.12)

3-(2-trifluoromethylbenzyl)-2,4,5-trioxoimidazolidine-1-acetic acid [Compound 54].
Melting point: 217.0°–219.0° C.
MS m/z: 262($M^+$)
IR(KBr): 3100(OH), 1720(C=O), 1445, 1425, 1310, 1180, 1150, 1105, 765 $cm^{-1}$
$^1$H-NMR(DMSO-$d_6$): 4.33(s,2H,N—$CH_2$—$CO_2$), 4.90(s, 2H,$CH_2$—N), 7.61–7.43 (m, 2H,Ar—H), 7.66 (dd, J=8.5, 7.0Hz, 1H,Ar—H), 7.78 (d,J=8.5Hz, 1H,Ar—H), 13.40 (brs, 1H, COOH)
Elementary analysis ($C_{13}H_9F_3N_2O_5$): Calculated (C=47.28, H=2.75,N=8.48), Found (C=47.35,H=2.84,N=8.40)

3-(3-trifluoromethylbenzyl)-2,4,5-trioxoimidazolidine-1-acetic acid [Compound 55].
Melting point: 190.0°–192.5° C.
MS m/z: 330($M^+$)
IR(KBr): 3000(OH), 1730(C=O), 1455, 1440, 1335, 1225, 1100 $cm^{-1}$
$^1$H-NMR (DMSO-$d_6$): 4.32(s, 2H,N—$CH_2$—$CO_2$), 4.87(s, 2H,$CH_2$—N), 7.60 (dd,J=7.5,7.5Hz, 1H,Ar—H), 7.64–7.72 (m, 2H,Ar—H), 7.74 (s, 1H,Ar—H), 13.44 (brs, 1H, COOH)
Elementary analysis ($C_{13}H_9F_3N_2O_5$): Calculated (C=47.28, H=2.75,N=8.48), Found (C=47.17,H=2.61,N=8.31)

3-(4-trifluoromethylbenzyl)-2,4,5-trioxoimidazolidine-1-acetic acid [Compound 56].
Melting point: 190.0°–192.0° F.
MS m/z: 330($M^-$)
IR(KBr): 3000(OH), 1715(C=O), 1440, 1325, 1140, 1065 $cm^{-1}$
$^1$H-NMR(DMSO-$d_6$): 4.29(s,2H,N—$CH_2$—$CO_2$), 4.85(s, 2H,$CH_2$—N), 7.58 (d,J=7.9Hz, 2H,Ar—H), 7.73 (d,J=7.9Hz, 2H,Ar—H), 13.45 (brs. 1H, COOH)
Elementary analysis ($C_3H_9F_3N_2O_5$): Calculated (C=47.28, H=2.75,N=8.48), Found (C=47.14,H=2.75,N=8.41)

3-(3-cyanobenzyl)-2,4,5-trioxoimidazolidine-1-acetic acid [Compound 57].
Melting point: 181.0°–181.5° C.
MS m/z: 287 ($M^+$)
IR(KBr): 3100(OH), 2231(CN), 1738(C=O), 1714(C=O), 1446, 1257, 1151 $cm^{-1}$
$^1$H-NMR(DMSO-$d_6$): 4.28 (s, 2H,N—$CH_2$—$CO_2$), 4.82 (s, 2H,$CH_2$—N), 7.58(dd,J=7.3,7.3Hz,1H,Ar—H),7.71(d,J=7.3Hz,1H,Ar—H), 7.78(d,J=7.3Hz,1H,Ar—H), 7.85(s, 1H,Ar—H), 13.48(brs,1H,COOH)
Elementary analysis ($C_{13}H_9N_3O_5$): Calculated (C=54.36, H=3.16, N=14.63 ), Found (C=54.36, H=3.13, N=14.57 )

3-(4-cyanobenzyl)-2,4,5-trioxoimidazolidine-1-acetic acid [Compound 58].
Melting point: 175.0°–176.0° C.
MS m/z: 287($M^+$)
IR(KBr): 3000(OH), 2250(CN), 1730(C=O), 1440, 1400, 1205, 760 $cm^{-1}$
$^1$H-NMR(DMSO-$d_6$): 4.30(s,2H,N—$CH_2$—$CO_2$), 4.85(s, 2H,$CH_2$—N), 7.56(d,J=7.9Hz,2H,Ar—H), 7.84(d,J=7.9Hz,2H,Ar—H), 13.41(brs.1H,COOH)
Elementary analysis ($C_{13}H_9N_3O_5$): Calculated (C=54.36,H=3.16,N=14.63), Found (C=53.98,H=3.24,N=14.42)

3-(3-carboxybenzyl)-2,4,5-trioxoimidazolidine-1-acetic acid [Compound 59].
Melting point: 244.5°–245.0° C.
MS m/z: 287 ($M^+$)
IR(KBr): 3000(OH), 1730(C=O), 1705(C=O), 1450, 1430, 1400, 1260, 1155 $cm^{-1}$
$^1$H-NMR(DMSO-$d_6$): 4.29(s,2H,N—$CH_2$—$CO_2$), 4.81(s, 2H,$CH_2$—N), 7.50(dd,J=8.0,8.0Hz,1H,Ar—H), 7.59(d,J=8.0Hz,1H,Ar—H), 7.88(d,J=8.0Hz,1H,Ar—H), 7.94(s, 1H,Ar—H), 13.14(brs,2H,COOH)
Elementary analysis ($C_{13}H_{10}N_2O_7$): Calculated (C=50.99, H=3.29,N=9.15), Found (C=50.87,H=3.40,N=9.08)

3-(3-carbamoylbenzyl)-2,4,5-trioxoimidazolidine-1-acetic acid [Compound 60].
Melting point: 234.5°–236.0° C.
IR(KBr): 3450($NH_2$), 3000(OH), 1730(C=O), 1450, 1425, 1400, 1145, 765 $cm^{-1}$
$^1$H-NMR(DMSO-$d_6$): 4.30(s,2H,N—$CH_2$—$CO_2$), 4.39(s, 2H,$CH_2$—N), 7.60–7.29(m,3H,Ar—H), 7.74(brs,2H, $NH_2$), 8.00(s,1H,Ar—H), 13.32 (brs, 1H, COOH)
Elementary analysis ($C_{13}H_{11}N_3O_6$): Calculated (C=51.15, H=3.63,N=13.77), Found (C=50.74,H=3.62,N=13.48)

3-(3-methoxycarbonylbenzyl)-2,4,5-trioxoimidazolidine-1-acetic acid [Compound 61].
Melting point: 89.0°–90.0° C. (decomp.)
MS m/z: 332 ($M^+$)
IR(KBr): 3100(OH), 1728(C=O), 1443, 1406, 1302, 1209, 1149, 756 $cm^{-1}$
$^1$H-NMR(DMSO-$d_6$): 3.86(s,3H,O—$CH_3$), 4.30(s,2H,N—$CH_2$—$CO_2$), 4.82(s,2H,$CH_2$—N), 7.52(dd,J=8.0,8.0Hz, 1H,O—C—Ar), 7.63(d,J=8.0Hz,2H,Ar—H), 7.90(d,J=8.0Hz,1H,Ar—H), 7.96(s,1H,Ar—H), 13.39(brs, 1H, COOH)
Elementary analysis ($C_{14}H_{12}N_2O_7$): Calculated (C=52.51, H=3.77,N=8.49) Found (C=52.60,H=3.77,N=8.49)

3-(4-chloro-3-nitrobenzyl)-2,4,5-trioxoimidazolidine-1-acetic acid [Compound 62].
Melting point: 178.0°–181.0° C.
MS m/z: 332(M$^+$)
IR(KBr): 3000(OH), 1730(C=O), 1710(C=O), 1535 (NO$_2$), 1435, 1345 (NO$_2$), 1255, 1145 cm$^{-1}$
$^1$H-NMR(DMSO-d$_6$): 4.29 (s,2H,N—CH$_2$—CO$_2$), 4.86(s, 2H,CH$_2$—N), 7.70(dd,J=8.0,1.5Hz,1H,Ar), 7.78(d,J=8.0Hz,1H,Ar—H), 8.06(d,J=1.5Hz,1H,Ar—H)
Elementary analysis (C$_{12}$H$_8$ClN$_3$O$_7$): Calculated (C=42.19, H=2.36,N=12.30), Found (C=42.10,H=2.37,N=12.26)

EXAMPLE 5

Compounds of the present invention were evaluated for pharmaceutical action and selectivity by measuring the rate of inhibition towards an aldose reductase and towards an aldehyde reductase:

(1) Inhibitory Action Towards Aldose Reductase

Action of the compounds of the present invention for inhibiting an aldose reductase was investigated using the aldose reductase which was prepared from lenses of rats. Thus, a compound was added to a reaction system comprising a phosphate buffer, NADPH (β-nicotinamide adenine dinucleotide phosphate, reduced form) and aldose reductase. After confirming for several minutes that the absorbencies became stable, glyceraldehyde was added thereto and a decrease in the absorbance at 340 nm with a lapse of time was measured whereby the inhibitory action of the compound to the aldose reductase was determined.

Examples of the results are given in Table 1 in which the inhibiting rate to the aldose reductase is the value when the concentration of the compound was 1×10$^{-7}$M:

TABLE 1

| Compound No. | Inhibiting rate | Compound No. | Inhibiting rate |
| --- | --- | --- | --- |
| Compound 32 | 58% | Compound 47 | 33% |
| Compound 41 | 42% | Compound 48 | 71% |
| Compound 42 | 27% | Compound 49 | 58% |
| Compound 43 | 42% | Compound 50 | 83% |
| Compound 44 | 26% | Compound 51 | 63% |
| Compound 45 | 60% | Compound 53 | 32% |
| Compound 46 | 48% | Compound 62 | 66% |

It is clear from the above-mentioned results of the pharmacological tests, that the parabanic acid derivatives of the present invention exhibit an excellent inhibitory action towards aldose reductase with a low toxicity whereby they are very useful as therapeutic agents for diabetic complications. Thus, they are useful as drugs for therapy and prevention of various types of diabetic complications caused by an excessive accumulation of intracellular sorbitol such as diabetic neuropathy, diabetic cataract and retinopathy, diabetic nephropathy, diabetic dermopathy and other diabetic microangiopathy.

2. Inhibitory Action Towards Aldehyde Reductase

The inhibitory action of the compounds of the present invention to an aldehyde reductase obtained from rat kidney was measured using the compounds at a concentration of 1×10$^{-4}$M but the inhibition was hardly noted. Thus, the compounds of the present invention having a high enzyme selectivity to aldose reductase participating in the production of sorbitol which induces diabetic complications exhibit low toxicity and high safety. Therefore, they are particularly useful for the therapy of the above-mentioned chronic diseases which require administration of a drug for a prolonged period.

The compounds of the present invention can be made into pharmaceutical preparations by combining one or more of the compounds with at least one pharmaceutical carrier or diluent. They can be made into various types of preparations by known methods. The compounds of the invention can be made into solid, semisolid, liquid or aerosol formulations for administration by oral or parenteral means.

The compounds of the present invention may be used either solely or jointly in pharmaceutically effective amounts for treating animals or humans. They may also be used in pharmaceutically effective amounts in combination with pharmaceutically effective amounts of other pharmaceutically active components in pharmaceutical compositions or preparations.

In the case of preparations for oral administration, one or more of the compounds of the present invention alone or together with commonly-used pharmaceutically acceptable excipients in pharmaceutically acceptable amounts such as a suitable pharmaceutically acceptable additive or carrier (e.g. lactose, mannitol, corn starch, potato starch, etc.) may be mixed with one or more pharmaceutically acceptable: (1) binders such as crystalline cellulose, cellulose derivatives, gum arabicum, corn starch, gelatin, etc., (2) disintegrating agents such as corn starch, potato starch, potassium carboxymethylcellulose, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

Alternatively, suppositories may be prepared by mixing at least one compound of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of parenteral administration using injections, for example, it is possible to prepare solutions or suspensions of one or more compounds of the present invention in pharmaceutically acceptable carriers such as aqueous and nonaqueous solvents such as distilled water for injection, physiological saline solution, Ringer's solution, plant oil, synthetic fatty acid glycerides, higher fatty acid esters, propylene glycol, etc.

In the case of inhalations or aerosol preparations, at least one compound of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

In order to make the compounds of the present invention into collyriums, they can be prepared as a solution or suspension together with an aqueous solvent such as sterile, purified water and physiologically saline solution, or a non-aqueous solvent for injection. The collyriums may also include pharmaceutically acceptable preservants, sterilizing agents, pH adjusting agents, and the like.

It is also possible, depending upon the type of the disease, to prepare pharmaceutical preparations other than the above-mentioned ones such as ointments, poultices, etc. which are most suitable for therapy depending upon the state of the patient and the type of disease.

The preferred dosage of the compound of the present invention varies depending upon the subject to be administered (age, body weight, symptoms, etc. of the patient), form of the preparation, method for the administration, treatment for the administration, etc. To achieve the desired result, the compound may be usually administered by the oral route with a daily dose of 10–3,000 mg, preferably 20–1,500 mg per day, to common adults.

In the case of parenteral administration such as by injection, the preferred dosage may be from one-third to one-tenth of the above-mentioned oral dosage because of the effects of absorption, etc. in the oral route.

We claim:

1. A compound which is a parabanic acid derivative represented by the formula (I) or a pharmaceutically acceptable salt thereof:

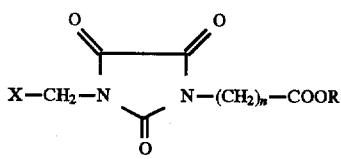

wherein

R is hydrogen, lower alkyl or benzyl;

X is benzothiazolyl which may be substituted with at least one member selected from the group consisting of lower alkyl, lower alkoxy, trifluoromethyl, nitro, and halogen, naphthyl which may be substituted with nitro and/or substituted with halogen, anthraquinonyl, phthalimide, or thienyl; and n is an integer from 1 to 3.

2. A compound according to claim 1 wherein R is lower alkyl.

3. A compound according to claim 1 wherein n is 1.

4. A compound according to claim 1 wherein X is a benzothiazolyl group substituted with at least one member selected from the group consisting of lower alkyl, lower alkoxy, trifluoromethyl, nitro, and halogen.

5. A compound according to claim 4 wherein said benzothiazolyl group is substituted with nitro and/or halogen.

6. A compound according to claim 4 wherein said benzothiazolyl group is substituted with halogen.

7. A compound according to claim 1 wherein X is naphthyl which may be substituted with nitro and/or substituted with halogen.

8. A compound according to claim 1 wherein X is a chlorobenzothiazolyl group, and R is hydrogen.

9. A compound according to claim 1 which is a pharmaceutically acceptable salt of the parabanic acid derivative represented by the formula (I).

10. A pharmaceutical composition for diabetic complications comprising a pharmaceutically acceptable carrier, and a pharmaceutically effective amount of at least one parabanic acid derivative represented by the formula (I) or a pharmaceutically acceptable salt thereof:

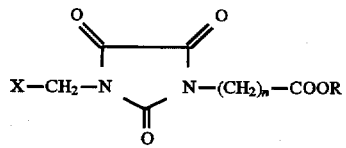

wherein

R is hydrogen, lower alkyl or benzyl;

X is benzothiazolyl which may be substituted with at least one member selected from the group consisting of lower alkyl, lower alkoxy, trifluoromethyl, nitro, and halogen, naphthyl which may be substituted with nitro and/or substituted with halogen, anthraquinonyl, phthalimide, or thienyl; and n is an integer from 1 to 3.

11. A pharmaceutical composition according to claim 10 wherein R is lower alkyl.

12. A pharmaceutical composition according to claim 10 wherein n is 1.

13. A pharmaceutical composition according to claim 10 wherein X is a benzothiazolyl group substituted with at least one member selected from the group consisting of lower alkyl, lower alkoxy, trifluoromethyl, nitro, and halogen.

14. A method of producing a parabanic acid derivative represented by the general formula (I)

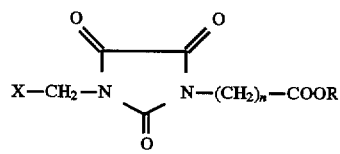

wherein

R is hydrogen, lower alkyl or benzyl;

X is benzothiazolyl which may be substituted with at least one member selected from the group consisting of lower alkyl, lower alkoxy, trifluoromethyl, nitro, and halogen, naphthyl which may be substituted with nitro and/or substituted with halogen, anthraquinonyl, phthalimide, or thienyl; and n is an integer from 1 to 3, comprising condensing a compound represented by the general formula (II):

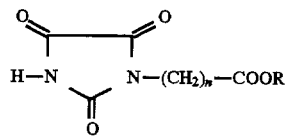

wherein R and n are defined as above, with a compound represented by the general formula (III):

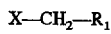 (III)

wherein X is defined as above, and $R_1$ is hydroxyl, halogen, lower alkyl—$SO_2$—O—, or phenyl—$SO_2$—O— which may be substituted with lower alkyl.

15. A method according to claim 14 wherein the condensate obtained by condensing said compound represented by general formula (II) with said compound represented by general formula (III) is subjected to hydrolysis.

16. A method according to claim 14 wherein R is lower alkyl.

17. A method according to claim 14 wherein n is 1.

18. A method according to claim 14 wherein X is a benzothiazolyl group substituted with at least one member selected from the group consisting of lower alkyl, lower alkoxy, trifluoromethyl, nitro, and halogen.

19. A method for the treatment of diabetic complications caused by excessive accumulation of intracellular sorbitol comprising administering a pharmaceutically effective amount of at least one compound according to claim 1 to substantially inhibit aldose reductase without substantially inhibiting aldehyde reductase.

* * * * *